United States Patent [19]

Gaffar et al.

[11] Patent Number: 5,605,676
[45] Date of Patent: Feb. 25, 1997

[54] ORAL COMPOSITION EXHIBITING IMPROVED UPTAKE AND RETENTION OF ANTIBACTERIAL COMPOUNDS ON DENTAL TISSUE SURFACES

[75] Inventors: Abdul Gaffar, Princeton; Nuran Nabi, Cranbury, both of N.J.

[73] Assignee: Colgate-Palmolive Company, New York, N.Y.

[21] Appl. No.: 494,744

[22] Filed: Jun. 26, 1995

[51] Int. Cl.$^6$ ........................................... A61K 7/16
[52] U.S. Cl. ................................. 424/49; 424/57
[58] Field of Search ........................... 424/49–58

[56] References Cited

U.S. PATENT DOCUMENTS

| | | | |
|---|---|---|---|
| 3,629,477 | 12/1971 | Model et al. | 424/340 |
| 4,022,880 | 5/1977 | Vinson et al. | 424/49 |
| 4,139,485 | 2/1979 | Imokawa et al. | 252/135 |
| 4,152,421 | 5/1979 | Tsutsumi et al. | 424/57 |
| 4,435,380 | 3/1984 | Pader | 424/49 |
| 4,871,396 | 10/1989 | Tsujita et al. | 424/49 |
| 4,980,153 | 12/1990 | Jackson et al. | 424/52 |
| 5,015,471 | 5/1991 | Birtwistle et al. | 424/70 |
| 5,019,373 | 5/1991 | Carter et al. | 424/52 |
| 5,112,613 | 5/1992 | Honda et al. | 424/400 |
| 5,139,781 | 8/1992 | Birtwistle et al. | 424/57 |
| 5,180,579 | 1/1993 | Birtwistle et al. | 424/57 |
| 5,370,865 | 12/1994 | Yamagishi et al. | 424/54 |
| 5,374,418 | 12/1994 | Oshino et al. | 424/54 |

*Primary Examiner*—Shep K. Rose
*Attorney, Agent, or Firm*—Paul Shapiro

[57] ABSTRACT

The invention provides an antibacterial oral composition containing an antibacterial compound such as Triclosan and a monoalkyl phosphate compound whereby the uptake and retention of the antibacterial compound on dental tissue is substantially increased due to the presence of the monoalkyl phosphate compound.

14 Claims, No Drawings

ORAL COMPOSITION EXHIBITING IMPROVED UPTAKE AND RETENTION OF ANTIBACTERIAL COMPOUNDS ON DENTAL TISSUE SURFACES

BACKGROUND OF THE INVENTION

1. Field of the Invention

The present invention relates to oral care compositions which are designed to improve the effectiveness of antibacterial compounds in the retardation and prevention of bacterial plaque accumulation on the teeth.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example, halogenated hydroxydiphenyl ether compounds such as Triclosan are well known to the art for their antibacterial activity and have been used in oral compositions to counter plaque formation by bacterial accumulation in the oral cavity.

Although antibacterial agents such as Triclosan are highly effective in killing bacteria which are responsible for plaque formation, it is difficult to maintain an effective level of such agents on dental tissue for a significant time period after their application. Thus, once applied, it is important that the antibacterial compound be maintained in continuing adherence to the teeth and adjacent oral gingival mucosa thereby retarding washout of the antibacterial compound from infected areas of dental tissue by saliva present in the mouth. This allows for a sufficient amount of compound to remain in contact with the dental tissue and achieve a protracted and effective therapeutic effect.

There is therefore a need in the art to provide means whereby antibacterial compounds contained in oral care compositions can be delivered to and retained on dental tissue for extended periods of time with reduced salivary washout.

SUMMARY OF THE INVENTION

In accordance with this invention there is provided an oral composition comprising in an orally acceptable vehicle, an effective antiplaque amount of an halogenated diphenyl ether or phenolic antibacterial compound, and an amount of a monoalkyl phosphate compound effective to enhance the delivery of said antibacterial compound to, and retention thereof on, oral surfaces whereby washout of the antibacterial agent is diminished so as to enhance the therapeutic efficacy of the administered compound.

DETAILED DESCRIPTION OF THE PREFERRED EMBODIMENTS

The present invention is based on the discovery that the presence of relatively low concentrations, e.g., about 0.1 to about 5% by weight of a monoalkyl phosphate compound in an oral composition containing an antibacterial halogenated diphenyl ether or phenolic compound substantially increases uptake and retention of the antibacterial compound on dental tissue.

The term "oral composition" is used herein to designate products which, in the ordinary course of usage, are retained in the oral cavity for a time sufficient to contact substantially all of the dental surfaces but are not intentionally ingested. Such products include, for example, dentifrices, gels, mouthwashes, chewing gums and lozenges.

Halogenated diphenyl ether antibacterial compounds for use in the oral care compositions of the present invention particularly desirable from considerations of antiplaque effectiveness and safety include 2,4,4'-trichloro-2'-hydroxydiphenyl ether (Triclosan) and 2,2'-dihydroxy-5,5'-dibromodiphenyl ether.

Phenolic compounds useful in the practice of the present invention include phenol and its homologs, mono and polyalkyl and aromatic halophenols, resorcinol and its derivatives and bisphenolic compounds, such phenolic compounds being more fully disclosed in U.S. Pat. No. 5,368,844 the disclosure of which is incorporated herein by reference. Preferred phenolic compounds are n-hexyl resorcinol and 2,2'-methylene bis (4-chloro- 6-bromophenol).

The halogenated diphenyl ether or phenolic antibacterial compound is present in the oral composition of the present invention in an effective antiplaque amount, typically about 0.05%–2.0% by weight, and preferably about 0.1%–1% by weight of the oral composition.

The term "monoalkyl phosphate compound" includes within its meaning a monoalkyl or monoalkenyl phosphate, mixtures thereof, and a salt thereof having the formula

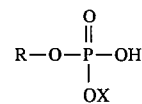

wherein R is an alkyl or alkenyl group having 6 to 18 carbon atoms and X is hydrogen, sodium, potassium or ammonium.

Monoalkyl phosphate compounds useful in the practice of the present invention include monolauryl phosphate, monooctyl phosphate, sodium lauryl phosphate and sodium monooctyl phosphate.

Monoalkyl phosphate compounds are known to the art and are used in combination with dialkyl phosphates in skin care compositions, e.g., U.S. Pat. No. 4,139,485 and as surfactants (U.S. Pat. No. 4,139,485, U.S. Pat. Nos. 4,152, 421 and 4,350, 680). Combinations of mono- and dialkyl phosphate salt have been disclosed as having efficacy as anti-caries agents (U.S. Pat. No. 5,019,373). Japanese Patent 6271440 discloses an antimicrobial compound of the formula Am+ Xm– wherein Am+ is a nitrogen containing antimicrobial agent and X– is an 8 to 20 carbon monoalkyl or monoalkenyl phosphoric acid ion and m is the valence of cation A. There is no suggestion in the art that monoalkyl phosphate compounds particularly when used alone, have any efficacy as enhancing the uptake and retention of halogenated diphenyl ether or phenolic antibacterial agents on dental tissue.

The monoalkyl phosphate compound, particularly when used alone and free of any dialkyl phosphate compound is found to enhance uptake and retention of halogenated diphenyl ether and phenolic antibacterial compounds on dental tissue when incorporated in the oral composition in amounts effective to achieve such enhancement, such amounts being within the range of about 0.05 to about 2% by weight and preferably about 0.1% to about 1%, by weight of the oral composition. As will hereinafter be demonstrated, the presence of these amounts of the monoalkyl phosphate compound in the oral composition increases the uptake of the halogenated dipenyl ether antibacterial compound on dental tissue greater than 5.0 fold, when compared to similar oral care compositions in which the monoalkyl phosphate compound is absent.

In the preparation of a an oral care composition in accordance with the practice of the present invention, an orally acceptable vehicle including a water-phase with humectant is present. The humectant is preferably glycerine, sorbitol, and/or propylene glycol. Water is present typically in amount of at least about 10% by weight, generally about 25 to 70% by weight and the humectant concentration typically totals about 10–80% by weight of the oral composition.

Dentifrice compositions also typically contain polishing materials including crystalline silica, having a particle size of up to about 20 microns, such as available as Zeodent 115, silica gel or colloidal silica, complex amorphous alkali metal aluminosilicates, as well as sodium bicarbonate, calcium carbonate, calcium pyrophosphate, dicalcium phosphate and alumina.

Dentifrices prepared in accordance with the present invention typically contain a natural or synthetic thickener in proportions of about 0.1 to about 5% by weight, preferably about 0.5 to about 2% by weight. Suitable thickeners include Irish moss, i-carrageenan, gum tragacanth, starch, polyvinylpyrrolidone, hydroxyethypropyl cellulose, hydroxybutyl methyl cellulose, hydroxypropyl methylcellulose, hydroxyethyl cellulose sodium carboxymethyl cellulose (NaCMC), and colloidal silica such as those available as finely ground Syloid 244 and Sylodent 15.

The oral composition may also contain a source of fluoride ions, or fluoride-providing compound, as an anti-caries agent, in an amount sufficient to supply about 25 ppm to 5,000 ppm of fluoride ions and preferably 500 to 1500 ppm fluoride ions. Among these compounds are inorganic fluoride salts, such as soluble alkali metal salts, for example, sodium fluoride, potassium fluoride, sodium fluorosilicate, ammonium flourosilicate and sodium monofluorphosphate, as well as tin fluorides, such as stannous fluoride and stannous chloride.

Any suitable flavoring or sweetening material may also be employed. Examples of suitable flavoring constituents include flavoring oils, e.g. oil of spearmint, peppermint, wintergreen, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine methyl ester), saccharine and the like. Suitably, flavor and sweetening agents may each or together comprise from about 0.1% to 5% more of the oral care composition. Moreover, flavor oil is believed to aid the dissolving of water insoluble non-cationic halogenated diphenyl ether anti-bacterial agents such as triclosan.

Various other materials may be incorporated in the oral preparations of this invention such as whitening agents, including urea peroxide, calcium peroxide, and hydrogen peroxide, preservatives, vitamins such as vitamin B6, B12, E and K, silicones, chlorophyll compounds, potassium salts for the treatment of dental hypersensitivity such as potassium nitrate as well as antitartar agents such as sodium tripolyphosphate and di- and tetraalkali metal pyrophosphate salts such as di- and tetrasodium pyrophosphate. These agents, when present, are incorporated in the compositions of the present invention in amounts which do not substantially adversely affect the properties and characteristics desired.

The following examples are further illustrative of the nature of the present invention, but it is understood that the invention is not limited thereto. All amounts and proportions referred to herein and in the appended claims are by weight, unless otherwise indicated.

EXAMPLE I

The effect of a monoalkyl phosphate compound as the sole alkyl phosphate compound when present in an oral composition on the uptake and retention to tooth surfaces of a halogenated diphenyl ether antibacterial agent was assessed using disks of saliva coated hydroxyapatite (SCHAP), the mineral phase of dental enamel, as an in vitro experimental model for human teeth. The in vitro assessment has been found to be correlatable to in vivo delivery of and retention of antibacterial agents on oral surfaces.

For the test of delivery of an antibacterial agent to a SCHAP disk, hydroxyapatite (HAP) is washed extensively with distilled water, collected by vacuum filtration, and dried overnight at 37° C. The dried HAP is ground into a powder with a mortar and pestle and 150 milligrams (mgs) of the powder is placed into a chamber of a KBr pellet die (Barnes Analytical, Stanford, Conn.). The HAP powder is compressed for 6 minutes at 10,000 pound in a Carver Laboratory press to prepare 13 mm diameter disks which are sintered for 4 hours at 800° C. in a Thermolyne furnace. Parafilm stimulated whole saliva is collected into an ice-chilled glass beaker and the saliva is clarified by centrifugation at 15,000 Xg (times gravity) for 15 minutes at 4° C. Sterilization of the clarified-saliva is done at 4° C. with stirring by irradiation of the sample with UV light for 1.0 hour.

Each sintered HAP disk is hydrated with sterile water in a polyethylene test tube. The water is then removed and replaced with 2 milliliters (ml) of saliva. A salivary pellicle is formed by incubating the disk overnight at 37° C. with continuous shaking in a water bath. After this treatment, the saliva is removed and the disks treated with 1.0 ml of a slurry or liquid phase solution of an oral care composition containing an antibacterial agent, the composition being diluted with water at a 1:1 ratio. The disks are then incubated at 37° C. with continuous shaking in the water bath. After 30 minutes, the disk is transferred into a new tube and 5 ml of water are added followed by shaking the disk gently with a Vortex. The disk is then transferred to a new tube and the washing procedure repeated twice. Finally, the disk is transferred to a new tube to avoid co-transfer of any liquid along with the disk. Then 1.0 ml of methanol is added to the disk and shaken vigorously with a Vortex. The sample is left at room temperature for 30 minutes to extract the absorbed antibacterial agent into the methanol. The methanol is then aspirated and clarified by centrifugation at 10,000 rpm to 5 minutes. After this treatment, the methanol is transferred into HPLC (high performance liquid chromatography) vials for determination of the concentration of antibacterial agent present. Triplicate samples were used in all tests.

To determine the delivery and retention of Triclosan to a SCHAP disk from a dentifrice containing triclosan and sodium lauryl phosphate (SLP) prepared in accordance with the practice of the present invention, a series of SCHAP disks was treated with a dentifrice slurry prepared from Composition A which contained the ingredients listed in Table I below. After incubation for 30 minutes at 37° C., the SCHAP disks were removed from the dentifrice slurry, washed twice with water, and then reincubated with 1.0 mil of parafilm stimulated human whole saliva which had been clarified by centrifugation. After incubation at 37° C. with constant shaking for 0, 1 hour and 4 hour time periods, the SCHAP disks were removed from the saliva, and the amount of Triclosan retained on the disks was determined by HPLC. The uptake and retention of Triclosan of Composition A on SCHAP disks is set forth in Table II below.

For purposes of comparison, the procedure of Example I was repeated except that sodium lauryl sulfate (SLS) was substituted for SLP in Composition A and designated Composition B. For purposes of further comparison, the procedure of Example I was repeated with the exception that dentifrice slurry designated Composition C containing a combination of 1.5% SLS and 2% Gantrez S-97 (a polycarboxylate compound comprised of a vinyl ether/maleic acid copolymer known to enhance uptake and retention of Triclosan to SCHAP disks as well as human teeth) was substituted for 1.5% SLP in Composition A. The uptake and retention of Triclosan from these comparative compositions B and C (the ingredients of which are listed in Table I) is set forth in Table II below.

TABLE I

| Composition | A Wt. % | B Wt % | C Wt. % |
|---|---|---|---|
| Ingredients: | | | |
| Sorbitol | 20.000 | 20.000 | 20.000 |
| Glycerol | 20.000 | 20.000 | 20.000 |
| Propylene Glycol | 0.500 | 0.500 | 0.500 |
| Sodium Lauryl Sulphate | 0.000 | 1.5000 | 1.500 |
| Sodium Lauryl Phosphate | 1.500 | 0.000 | 0.000 |
| Gantrez S-97 (12.8%) | 0.000 | 0.000 | 15.625 |
| Triclosan | 0.300 | 0.300 | 0.300 |
| NaF | 0.243 | 0.243 | 0.243 |
| Water | 56.457 | 56.457 | 40.232 |
| Flavor Oil | 1.000 | 1.00 | 1.000 |
| NaOH (50%) | 0.000 | 0.000 | 0.600 |
| pH | 7.00 | 7.00 | 7.00 |
| TOTAL | 100.000 | 100.00 | 100.000 |

TABLE II

| | Triclosan Uptake & Retention *Ug/Disk) Washing Time with Saliva (Hours) | | |
|---|---|---|---|
| COMPOSITION | 0.00 Hours | 1.0 Hours | 4.0 Hours |
| A(1.5% SLP) | 210.78 +/− 11.2 | 208.00 +/− 16.8 | 223.37 +/− 22.8 |
| B(1.5% SLS) | 38.28 +/− 3.6 | 27.62 +/− 2.0 | 21.82 +/− 3.1 |
| C(1.5% SLS + 15.6% Gantrez) | 97.23 +/− 4.0 | 83.08 +/− 8.9 | 87.25 +/− 4.8 |

The results recorded in Table II show that the delivery and retention of Triclosan to SCHAP disks from a dentifrice slurry was enhanced 5.5 fold by the presence in the dentifrice of SLP (Composition A) as compared to a dentifrice in which SLS was the surfactant (Composition B) and 2.16 fold increase compared to a dentifrice which contained a combination of SLS and Gantrez (Composition C).

For the purposes of still further comparison, the procedure of Example I was repeated to prepare a series of dentifrice slurries using a combination of SLP and SLS of varying concentrations as the surfactant as well as SLP and SLS as the sole surfactant.

The uptake and retention of Triclosan of the dentifrice compositions designated D, E, F, G and H on SCHAP disks not exposed to washing with saliva is recorded in Table III below.

TABLE III

| Composition | SLP Wt % | SLS Wt % | Triclosan Uptake (Ug/Disk) |
|---|---|---|---|
| D | 1.5 | 0.0 | 226.0 +/− 15.6 |
| E | 1.0 | 0.5 | 169.96 +/− 14.4 |
| F | 0.75 | 0.75 | 146.28 +/− 7.6 |
| G | 0.5 | 1.0 | 105.32 +/− 9.9 |
| H | 0.0 | 1.5% | 38.28 +/− 3.6 |

The results in Table III show that when SLS was present in dentifrices containing SLP, uptake of triclosan to SCHAP disks was inhibited in a dose response manner.

The effect of a combination of a monoalkyl phosphate such as monolauryl phosphate (MAP) and a dialkyl phosphate such as di(2-ethylhexyl) phosphoric acid (DEHPA) and 2-ethylhexyl acid phosphate (2-EHAPO4) on triclosan uptake to SCHAP disks was investigated. Dentifrice slurries were prepared following the procedure of Example I with MAP, DEHPA or 2-EHAPO4 or a combination of these compounds as surfactants. The pH of the slurries were adjusted to 7.0 by adding NaOH. The results are summarized in Table IV.

TABLE V

| Composition | Surfactants | Triclosan Uptake (ug/Disk) |
|---|---|---|
| I | 1.5% MAP | 231.58 +/− 29.9 |
| J | 1.5% DEHPA | 43.97 +/− 20.4 |
| K | 1.5% 2-EHAPO4 | 49.04 +/− 11.5 |
| L | 1.5% MAP/1.5% DEHPA | 166.56 +/− 12.8 |
| M | 0.75% MAP/0.75% DEPHA | 169.43 +/− 32.4 |
| N | 1.5% MAP/1.5% 2-EHAPO4 | 129.90 +/− 13.3 |
| O | 0.75% MAP/0.75% 2-EHAPO4 | 156.2 +/− 7.8 |

The data recorded in Table IV show that MAP (Composition I) provided about 5 times the triclosan uptake when compared to the uptake of the dialkyl phosphates DEHPA and 2-EHAPO4 (Compositions J and K) of the same concentration. The combination of MAP and DEHPA or 2-EHAPO4 (Compositions L–O) did not enhance but rather inhibited the triclosan uptake to SCHAP disks when compared to MAP alone.

EXAMPLE II

A toothpaste prepared in accordance with the present invention has the following composition.

| Ingredients | % (weight/weight) |
|---|---|
| Sorbitol | 20.0 |
| Glycerol | 20.0 |
| Propylene Glycol | 0.5 |
| Zeodent 115 | 20 |
| Sylodent 15 | 1.5 |
| Alkyl phosphate | 1.5 |
| Sodium Fluoride | 0.243 |
| NaCMC | 1.1 |
| Iota Carageenan | 0.4 |
| Sodium Saccharin | 0.3 |
| TiO2 | 0.5 |
| Triclosan | 0.3 |

EXAMPLE III

-continued

| Ingredients | % (weight/weight) |
|---|---|
| Flavor Oil | 1.0 |
| Water | 32.657 |
| Total | 100.00 |

EXAMPLE III

A mouthrinse prepared in accordance with the present invention has the following composition.

| Ingredients | % (weight/weight) |
|---|---|
| Propylene glycol | 7.0 |
| Triclosan | 0.03 |
| Ethanol (96%) | 9.84 |
| Flavor | 1.145 |
| Sodium fluoride | 0.025 |
| Disodium phosphate (anhydrous) | 0.05 |
| Sodium lauryl phosphate | 0.40 |
| Sorbitol (70%) | 15.0 |
| Glycerin (99%) | 5.0 |
| Water | 62.505 |
| Total | 100.00 |

What is claimed is:

1. In an antibacterial oral composition containing an effective therapeutic amount of a halogenated diphenyl ether or phenolic antibacterial compound the improvement consisting essentially of a monoalkyl phosphate compound present in an amount effective to increase the uptake of the antibacterial compound by dental tissue.

2. The composition of claim 1 wherein the antibacterial agent is incorporated in the composition at a concentration of about 0.05 to about 2.0% by weight.

3. The composition of claim 1 wherein the antibacterial agent is triclosan.

4. The composition of claim 1 wherein the monoalkyl phosphate compound is incorporated in the composition at a concentration of about 0.1 to about 5% by weight.

5. The composition of claim 1 wherein the monoalkyl phosphate compound has the formula

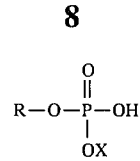

where R is an alkyl or alkenyl group having 6 to 18 carbon atoms and X is hydrogen, sodium, potassium or ammonium.

6. The composition of claim 1 wherein the monoalkyl phosphate compound is sodium lauryl phosphate.

7. The composition of claim 1 wherein the monoalkyl phosphate compound is monolauryl phosphate.

8. In a method for the treatment and prevention of bacterial plaque accumulation on teeth by administering to the oral cavity an oral composition containing an effective therapeutic amount of a halogenated diphenyl ether or phenolic antibacterial compound wherein the improvement consists essentially of providing a monoalkyl phosphate compound as the sole alkyl phosphate in an amount effective to increase the uptake of the antibacterial compound by dental tissue.

9. The method of claim 8 wherein the antibacterial compound is Triclosan.

10. The method of claim 8 wherein the antibacterial compound is incorporated in the composition at a concentration of about 0.05 to about 2.0% by weight.

11. The method of claim 8 wherein the monoalkyl phosphate compound is incorporated in the composition at a concentration of about 0.1 to about 5% by weight.

12. The method of claim 8 wherein the monoalkyl phosphate compound has the formula

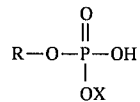

where R is an alkyl or alkenyl group having 6 to 18 carbon atoms and X is hydrogen, sodium, potassium or ammonium.

13. The method of claim 8 wherein the monoalkyl phosphate compound is sodium lauryl phosphate.

14. The method of claim 8 wherein the monoalkyl phosphate compound is monolauryl phosphate.

* * * * *